United States Patent [19]
Wittman et al.

[11] Patent Number: 5,489,589
[45] Date of Patent: Feb. 6, 1996

[54] AMINO ACID DERIVATIVES OF PACLITAXEL

[75] Inventors: Mark D. Wittman, Cheshire; John F. Kadow, Wallingford, both of Conn.

[73] Assignee: Bristol-Myers Squibb Company, Princeton, N.J.

[21] Appl. No.: 350,919

[22] Filed: Dec. 7, 1994

[51] Int. Cl.$^6$ .......... A61K 31/335; A61K 31/535; C07D 305/14; C07D 413/12

[52] U.S. Cl. .......... 514/232.8; 514/210; 514/253; 514/422; 514/449; 514/228.2; 544/147; 544/375; 544/58.7; 548/525; 548/950; 548/964; 549/510

[58] Field of Search .......... 544/147, 375; 549/510; 514/232.8

[56] References Cited

U.S. PATENT DOCUMENTS

| 4,942,184 | 7/1990 | Haugwitz et al. |
| 4,960,790 | 10/1990 | Stella et al. |
| 5,059,699 | 10/1991 | Kingston et al. |

FOREIGN PATENT DOCUMENTS

| 558959A1 | 9/1993 | European Pat. Off. |
| 569281A1 | 11/1993 | European Pat. Off. |
| 604910A1 | 7/1994 | European Pat. Off. |

OTHER PUBLICATIONS

Nicholas Bodor and James J. Kaminski, "Chapter 30. Prodrugs and Site-Specific Chemical Delivery Systems", Annual Reports In Medicinal Chemistry, 22, pp. 303–312, 1987.

H. M. Deutsch, et al, "Synthesis of Congeners and Prodrugs. 3.$_1$ Water–Soluble Prodrugs of Taxol with Potent Antitumor Activity", J. Med. Chem., 32, pp. 788–792, 1989.

Michael Hepperle and Gunda I. Georg, "Taxol Analogs", Drugs Of The Future, 19(6), pp. 573–584, 1994.

Abraham E. Mathew, et al, "Synthesis and Evaluation of Some Water–Soluble Prodrugs and Derivatives of Taxol with Antitumor Activity", J. Med Chem., 35, pp. 145–151, 1992.

Kyriacos C. Nicolaou, et al, "Chemistry and Biology of Taxol", Angew. Chem. Int. Ed. Engl., 33, pp. 15–44, 1994.

S. A. Varia, et al, "Phenytoin Prodrugs IV: Hydrolysis of Various 3–(Hydroxymethyl)phenytoin Esters", Journal Of Pharmaceutical Sciences, 73, No. 8, pp. 1074–1080, Aug., 1984.

Primary Examiner—Robert W. Ramsuer
Attorney, Agent, or Firm—William T. Han

[57] ABSTRACT

The present invention concerns water-soluble amino acid derivatives of paclitaxel, their use as antitumor agents, and pharmaceutical compositions containg the compounds.

11 Claims, No Drawings

AMINO ACID DERIVATIVES OF PACLITAXEL

BACKGROUND OF THE INVENTION

1. Field of the Invention

The present invention concerns antitumor compounds. More particularly, the invention provides novel taxane derivatives, pharmaceutical compositions thereof, and their use as antitumor agents.

2. Background Art

Taxol® (paclitaxel) is a natural product extracted from the bark of Pacific yew trees, Taxus brevifolia. It has been shown to have excellent antitumor activity in in vivo animal models, and recent studies have elucidated its unique mode of action, which involves abnormal polymerization of tubulin and disruption of mitosis. It has been recently approved for the treatment of ovarian cancer; and studies involving breast, colon, and lung cancers have shown promising results. The results of paclitaxel clinical studies are reviewed by Rowinsky and Donehower in "The Clinical Pharmacology and Use of Antimicrotubule Agents in Cancer Chemotherapeutics" *Pharmac. Ther.*, 52:35–84, 1991; and by K. C. Nicolaou et al. in "Chemistry and Biology of Taxol" *Angew. Chem., Int. Ed. Engl.*, 33:15–44, 1994, and also in the references cited therein.

Recently, a semi-synthetic analog of paclitaxel named Taxotere® has also been found to have good antitumor activity in animal models. Taxotere® is also currently undergoing clinical trials in Europe and the United States. The structures of paclitaxel and Taxotere® are shown below along with the conventional numbering system of taxane molecules; such numbering system is also employed in this application.

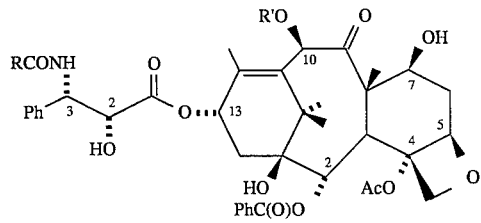

Taxol ®: R = Ph; R' = acetyl
Taxotere ®: R = t-butoxy; R' = hydrogen

One drawback of paclitaxel is its very limited water solubility. Accordingly, a number of research teams have prepared water-soluble derivatives, and some of them are disclosed in:

(a) Haugwitz et al., U.S. Pat. No. 4,942,184; Deutch et al., *J. Medicinal Chemistry*, 1989, 32, pp 788–792;

(b) Kingston et al., U.S. Pat. No. 5,059,699;

(c) Stella et al., U.S. Pat. No. 4,960,790; A. E. Mathew et al., *J. Medicinal Chemistry*, 1992, 35, pp 145–451;

(d) European Patent Application 558,959 published Sep. 8, 1993;

(e) European Patent Application 569,281 published Nov. 10, 1993; and (f) European Patent Application 604,910 published Jul. 7, 1994.

SUMMARY OF THE INVENTION

The present invention relates to water soluble taxane derivatives having the formula (I):

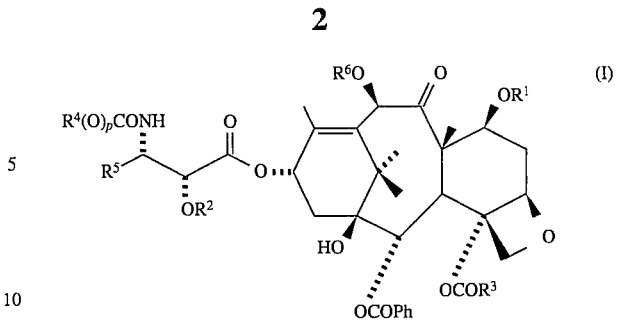

wherein $R^1$ or $R^2$ are independently hydrogen or —$CH_2O)_n COCH_2Y$; $R^6$ is hydrogen, $C_{1-8}$ alkanoyl or —$(CH_2O)_n COCH_2Y$; n is one to six; p is zero or one; $R^4$ and $R^5$ are independently $C_{1-8}$ alkyl, $C_{2-8}$ alkenyl, $C_{2-8}$ alkynyl, or —Z—$R^7$; Z is a direct bond, $C_{1-8}$ alkylene or $C_{2-8}$ alkenediyl; $R^7$ is aryl, substituted aryl, $C_{3-8}$ cycloalkyl or heteroaryl; $R^3$ is hydrogen, $C_{1-8}$ alkyl, $C_{2-8}$ alkenyl, $C_{2-8}$ alkynyl, $C_{3-8}$ cycloalkyl, aryl or heteroaryl; Y is a radical of the formula

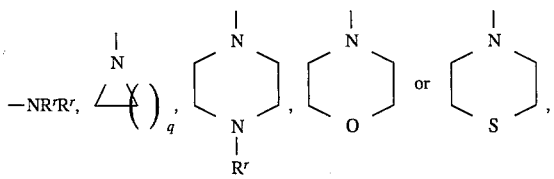

in which q is one to three; $R^r$ is hydrogen or $C_{1-8}$ alkyl; and with the proviso at least one of $R^1$, $R^2$ and $R^6$ is —$CH_2O)_n COCH_2Y$; or a pharmaceutically acceptable salt thereof.

Another aspect of the present invention provides a method for inhibiting tumor in a mammalian host which comprises administering to said mammalian host an antitumor effective amount of a compound of the formula (I).

Yet another aspect of the present invention provides a pharmaceutical composition (formulation) which comprises an antitumor effective amount of a compound of the formula (I) and a pharmaceutically acceptable carrier.

DETAILED DESCRIPTION OF THE INVENTION

In the present application, the numbers in the subscript after the symbol "C" define the number of carbon atoms a particular group can contain. For example, "$C_{1-8}$ alkyl" means a straight or branched saturated carbon chain having from one to eight carbon atoms; examples include methyl, ethyl, n-propyl, isopropyl, n-butyl, sec-butyl, isobutyl, t-butyl, n-pentyl, sec-pentyl, isopentyl, n-hexyl, n-heptyl, and n-octyl. "$C_{1-8}$ alkylene" means $C_{1-8}$ alkyl with two points of attachment; examples include methylene, ethylene, and propylene. "$C_{2-8}$ alkenyl" means a straight or branched carbon chain having at least one carbon-carbon double bond, and having from two to eight carbon atoms; examples include ethenyl, propenyl, isopropenyl, butenyl, isobutenyl, pentenyl, and hexenyl. "$C_{2-8}$ alkenediyl" refers to $C_{2-8}$ alkenyl with two points of attachment; examples include ethylene-1,2 -diyl (vinylene), 2-methyl-2-butene-1,4 -dinyl, 2-hexene-1,6-diyl, and the like groups. "$C_{2-8}$ alkynyl" means a straight or branched carbon chain having at least one carbon-carbon triple bond, and from two to eight carbon atoms; examples include ethynyl, propynyl, butynyl, and hexynyl. "$C_{1-8}$ alkanoyl" refers to groups such as formyl, acetyl, propanoyl, hexanoyl, etc.

"Aryl" means aromatic hydrocarbon having from six to ten carbon atoms; examples include phenyl and naphthyl. "Substituted aryl" means aryl substituted with at least one group selected from $C_{1-8}$ alkanoyloxy, hydroxy, halogen, $C_{1-8}$ alkyl, trifluoromethyl, $C_{1-8}$ alkoxy (alkyloxy), aryl, $C_{2-8}$ alkenyl, $C_{1-8}$ alkanoyl, nitro, amino, and amido. "Halogen" means fluorine, chlorine, bromine, and iodine.

"Methylthiomethyl" (also abbreviated as MTM) refers to the group $-CH_2SCH_3$.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

As used herein, hydroxy protecting groups are moieties which can be employed to block or protect the hydroxy function and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 2,2,2-trichloroethyoxymethyl, 2,2,2-trichloroethyloxycarbonyl, tetrahydropyranyl, tetrahydrofuranyl, t-butyl, benzyl, p-nitrobenzyl, p-methoxybenzyl, diphenylmethyl, tri$C_{1-6}$ alkylsilyl, triphenylsilyl, and the like. Preferred protecting groups for the 2'-hydroxy group of paclitaxel and a derivative thereof are triethylsilyl, 2,2,2-trichloroethyloxycarbonyl and benzyloxycarbonyl. Additional examples of hydroxy protecting groups may be found in standard reference works such as Greene and Wuts, *Protective Groups in Organic Synthesis*, 2d Ed., 1991, John Wiley & Sons, and McOmie, *Protective Groups in Organic Chemistry*, 1975, Plenum Press. Methods for introducing and removing protecting groups are also found in such textbooks.

"Taxane" denotes moieties containing the twenty carbon taxane core framework represented by the structural formula shown below with the absolute configuration.

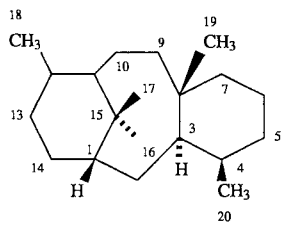

The numbering system shown above is one used in conventional taxane nomenclature, and is followed throughout the application. For example, the notation C1 refers to the carbon atom labelled as "1"; C5– C20 oxetane refers to an oxetane ring formed by the carbon atoms labelled as 4, 5 and 20 with an oxygen atom.

The synthesis of a compound of formula (I) can be accomplished by a wide variety of methods. The synthetic descriptions and specific examples that follow are only intended for the purpose of illustration, and are not to be construed as limiting in any manner ways to make compounds of the present invention by any other methods.

For example, a compound of formula (I) can be prepared by a process of Scheme I or an obvious variant thereof. In Scheme I, a compound of formula (II) is treated with chloroacetic acid or bromoacetic acid the presence of NIS with triflate as a catalyst to afford a compound of formula (III). (Step a). Preferred triflate is silver triflate or trialkylsilyltriflate. An analogous reaction of an alcohol with methylthiomethyloxy group in the presence of NIS was reported by Veeneman et al, in Tetrahedron. 1991 , 47, pp. 1547–1562, the relevant portions thereof are hereby incorporated by reference. In formula (II), $R^a$ and $R^c$ are independently, hydrogen, $-CH_2(OCH_2)_mSCH_3$ or a hydroxy protecting group; $R^b$ is $C_{1-8}$ alkanoyl, hydrogen, $-CH_2(OCH_2)_mSCH_3$ or a hydroxy protecting group; with the proviso at least one of $R^a$, $R^b$ and $R^c$ is $-CH_2(OCH_2)_mSCH_3$; and m is zero or an integer from 1to 5 inclusive. In formula (III), $R^d$ and $R^f$ are independently $-(CH_2O)_nCOCH_2D$ or hydrogen; $R^e$ is $C_{1-8}$ alkanoyl, $-(CH_2O)_nCOCH_2D$ or hydrogen; D is chloro or bromo; with the proviso at least one of $R^d$, $R^e$ and $R^f$ is $-(CH_2O)_nCOCH_2D$.

Subsequently a compound of formula (III) is reacted with an amine selected from the group consisting of

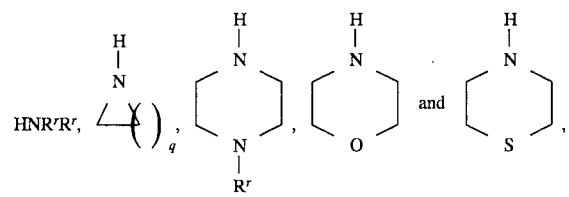

to afford a compound of formula (I). (Step b). In Step b, it is preferable to replace the chloro or the bromo radical in a formula (III) compound with iodine before reacting the compound with an amine, as illustrated by way of examples that follow. All other symbols used in connection with Scheme I are as defined earlier.

The syntheses of methylthiomethyl derivatives of formula (II) or other starting materials are described in detail in our European patent application 604,910 A1 published Jul. 6, 1994 which is herein incorporated by reference in its entirety. Other starting materials not specifically described in 604,910 A1 are reported elsewhere or can be readily obtained by anyone skilled in the art using conventional organic chemistry technique.

SCHEME I

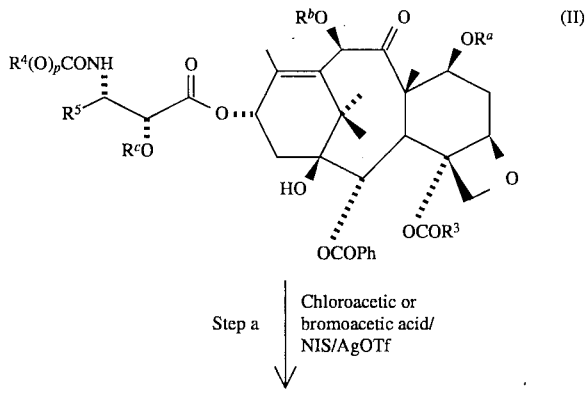

-continued
SCHEME I

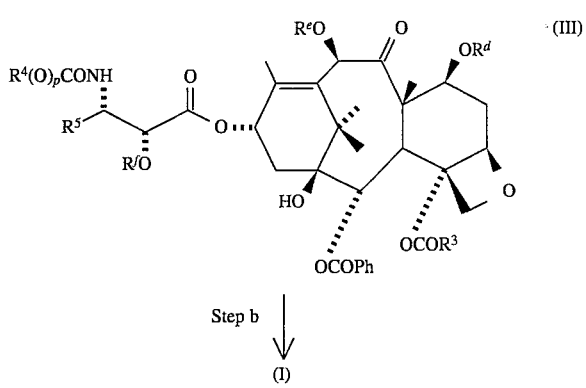

Step b ↓

(I)

Compounds of formula (I) of the instant invention are effective tumor inhibiting agents, and thus are useful in human and/or veterinary medicine. Thus, another aspect of the instant invention concerns a method for inhibiting human and/or other mammalian tumors which comprises administering to a tumor bearing host an antitumor effective amount of a compound of formula (I).

Compounds of formula (I) of the present invention may be used in a manner similar to that of paclitaxel; therefore, an oncologist skilled in the art of cancer treatment will be able to ascertain, without undue experimentation, an appropriate treatment protocol for administering a compound of the present invention. The dosage, mode and schedule of administration for compounds of this invention are not particularly restricted, and will vary with the particular compound employed. Thus a compound of the present invention may be administered via any suitable route of administration, preferably parenterally; the dosage may be, for example, in the range of about 1 to about 100 mg/kg of body weight, or about 20 to about 500 mg/m². The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical compositions (formulations) containing an antitumor effective amount of a compound of formula (I) in combination with one or more pharmaceutically acceptable carriers, excipients, diluents or adjuvants. Examples of formulating paclitaxel or derivatives thereof may be found in, for example, U.S. Pat. Nos. 4,960,790 and 4,814,470, and such examples may be followed to formulate the compounds of this invention. For example, compounds of the present invention may be formulated in the form of tablets, pills, powder mixtures, capsules, injectables, solutions, suppositories, emulsions, dispersions, food premix, and in other suitable forms. They may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

Compounds of formula (I) may form pharmaceutically acceptable acid addition salts. Said salts are those in which anion does not contribute significantly to the toxicity of the salt and are compatible with the customary pharmaceutical vehicles and adapted for oral or parenteral administration. The pharmaceutically acceptable acid addition salts include the salts of compounds of formula (I) with mineral acids such as hydrochloric acid, hydrobromic acid, phosphoric acid and sulfuric acid; with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, isethionic acid, p-tolenesulfonic acid and other acids know and used in the galenic pharmacy. Thus this invention further relates to a pharmaceutically acceptable salt of a compound of formula (I).

DESCRIPTION OF SPECIFIC EMBODIMENTS

The specific examples that follow illustrate the syntheses of representative compounds of the instant invention and their starting materials, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are: MS (mass spectrometry); HRMS (high resolution mass spectrometry); Ac (acetyl); Ph (phenyl); v/v (volume/volume); FAB (fast atom bombardment); NOBA (m-nitrobenzyl alcohol); rain (minute(s)); h or hr(s) (hour(s)); NIS (N-iodosuccinimide); BOC (t-butoxycarbonyl); CBZ or Cbz (benzyloxycarbonyl); Bn (benzyl); Bz (benzoyl); TES (triethylsilyl); DMSO (dimethylsulfoxide); THF (tetrahydrofuran); HMDS (hexamethyl disilazane).

EXAMPLE 1

3'-N-debenzoyl-3'-N-(t-butyloxycarbonyl)-7-O-methylthiomethylpaclitaxel

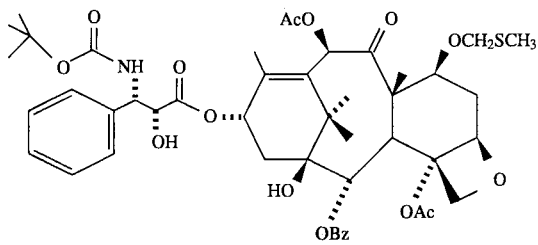

To a solution of hexamethyldisilazane (HMDS) (0.275 mL, 1.30 mmol) in 8 mL of THF was added a solution of n-BuLi (0.48 mL, 2.5M in hexanes, 1.20 mmol) and stirred 5 minutes at −55° C. To this solution was added 7-O-methylthiomethylbaccatin III, described in European patent application 604,910 published Jul. 6, 1994, (639 mg, 0.99 mmol) in 8 mL of THF and stirred for 10 minutes before addition of an 8 mL solution of (3R,4S)-1-butyloxycarbonyl-4-phenyl-3-triethylsilyloxy- 2-azetidinone (575 mg, 1.52 mmol) in THF. The cold bath was removed and replaced with a 0° C. bath and the reaction stirred for 30 minutes. The solution was diluted with ethyl acetate and washed with saturated $NH_4Cl$ solution, dried over $MgSO_4$ and concentrated. The residue was chromatographed over silica gel (3:1 hexane/ethyl acetate) to give 1.0 g of the coupling product 3'-N-debenzoyl-3'-N-(t-butyloxycarbonyl)-7-O-methylthiomethyl-2'-O-triethylsilylpaclitaxel (98%); 1H NMR ($CDCl_3$, 300 MHz) δ8.09 (d, J=6.9 Hz, 2H), 7.57 (m, 1H), 7.46 (t, J=7.8 Hz, 2H), 7.35 (m, 2H), 7.26 (m, 3H), 6.55 (s, 1H), 6.25 (t, J=9.6 Hz, 1H), 5.68 (d, J=6.9 Hz, 1H), 5.45 (br d, J= 9.3 Hz, 1H), 5.27 (br d, 1H), 4.95 (d, J=7.8 Hz, 1H), 4.65 (s, 2H), 4.53 (s, 1H), 4.29 (m, 2H), 4.17 (d, J=8.4 Hz, 1H), 3.89 (d, J=6.9 Hz, 1H), 2.81 (m, 1H), 2.51 (s, 3H), 2.37 (dd, J=15.3, 9.6 Hz, 1H), 2.17 (s, 3H), 2.10 (s, 3H), 2.03 (s, 3H), 1.85 (m, 1H), 1.74 (s, 3H), 1.63 (d, J=14.1 Hz, 1H), 1.29 (s, 9H), 1.21 (s, 6H), 0.76 (t, J=7.8 Hz, 9H), 0.36 (m, 6H); $^{13}C$ NMR ($CDCl_3$, 75.5 Hz) δ202.0, 171.6, 170.1, 169.3, 167.1, 155.2, 141.0, 139.0, 133.6, 132.8, 130.2, 129.2, 128.7, 128.5, 127.7, 126.4, 83.9, 81.2, 79.9, 78.9, 76.0, 75.7, 75.2, 74.8, 74.2, 71.3, 57.3, 56.7, 47.0, 43.3, 35.3, 33.0, 28.2, 26.4, 23.0, 21.5, 21.0, 15.0, 14.4, 10.9, 6.5, 4.3; IR(film) 3448 (s), 1720, 1242, 1120, 1056 $cm^{-1}$. FABMS (NOBA) M+Na calcd for $C_{52}H_{73}NSSiO_{15}$: 1046. Found: 1046.

To a solution of the silyl ether obtained above (269 mg, 0.26 mmol) in 6 mL of THF was added tetrabutylammonium fluoride (0.3 mL, 1.0M in THF, 0.3 mmol) and stirred 10 minutes. The solution was diluted with ethyl acetate and washed with brine, dried over $MgSO_4$ and concentrated and the residue was chromatographed over silica gel (1:1 hexane/ethyl acetate) to give 240 mg of the title compound (95%); 1H NMR ($CDCl_3$, 300 MHz) δ8.0 6 (d, J=7.2 Hz, 2H), 7.57 (t, J=7.2 Hz, 1H), 7.46 (t, J=7.8 Hz, 2H), 7.35 (m, 5H), 6.52 (s, 1H), 6.16 (t, J=8.7 Hz, 1H), 5.64 (d, J=6.9 Hz, 1H), 5.43 (br d, J=9.3 Hz, 1H), 5.24 (br d, J=8.1 Hz, 1H), 4.91 (d, J=8.1 Hz, 1H), 4.63 (m, 3H), 4.26 (m, 2H), 4.14 (d, J=8.4 Hz, 1H), 3.83 (d, J=6.9 Hz, 1H), 3.46 (d, J=5.4 Hz, 1H), 2.77 (m, 1H), 2.34 (s, 3H), 2.27 (m, 1H), 2.16 (s, 3H), 2.09 (s, 3H), 1.97 (s, 3H), 1.79 (m, 2H), 1.72 (s, 3H), 1.32 (s, 9H), 1.19 (s, 3H), 1.18 (s, 3H); $^{13}C$ NMR ($CDCl_3$, 75.5 Hz) δ202.0, 172.7, 170.3, 169.2, 167.0, 155.3, 140.3, 138.4, 133.7, 133.2, 130.2, 129.1, 128.8, 128.7, 128.0, 126.7, 83.9, 81.3, 80.2, 78.6, 76.5, 76.1, 75.4, 74.6, 74.0, 73.6, 72.3, 57.4, 56.1, 47.1, 43.2, 35.3, 32.8, 28.2, 26.5, 22.6, 21.0, 15.1, 14.6, 10.9; IR(film) 3440, 1720, 1370, 1242, 1170, 1108, 1066, 756 $cm^{-1}$. FABMS (NOBA) M+Na calcd for $C_{47}H_{59}NO_{15}SNa$: 932. Found: 932.

EXAMPLE 2

3'-N-Debenzoyl-3'-N-(n-butyloxycarbonyl)-7-O-methylthiomethylpaclitaxel

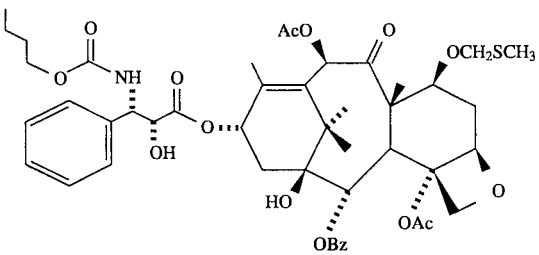

To a solution of 7-O-methylthiomethylbaccatin III (425 mg, 0.66 mmol) in 10 mL of THF at −60° C. was added nBuLi (0.30 mL, 2.5M, 0.75 mmol) and stirred for 10 min. (3R,4S)-3-Triethylsilyloxy-4-phenyl-N-(n-butyloxycarbonyl)azetidin- 2-one (350 mg, 0.93 mmol) in 6 mL of THF was added dropwise and then the reaction brought to 0° C. for 30 min. The solution was quenched with saturated $NH_4Cl$ and extracted with ethyl acetate, shaken with $Bu_4NF$ (1.0 mL, 1.0M, 1.0 mmol) and then washed with brine, dried over $MgSO_4$ and concentrated. The residue was chromatographed over silica gel (1.5:1 hexane/ethyl acetate) to give 581 mg of the title product which was crystalized from toluene/hexane to give 464 mg of a white solid (77%); IR(KBr) 3444, 1722, 1372, 1242, 1108, 1066, 1026, 988 $cm^{-1}$; 1H NMR ($CDCl_3$,300 MHz) δ8.08 (d, J=7.2 Hz, 2H), 7.59 (t, J=7.5 Hz, 1H), 7.47 (t, J=7.2 Hz, 2H), 7.39–7.11 (m, 5H), 6.51 (s, 1H), 6.20 (t, J=8.7 Hz, 1H), 5.65 (d, J=6.9 Hz, 1H), 5.56 (d, J=9.3 Hz, 1H), 5.29 (d J=8.4 Hz, 1H), 4.91 (d, J=8.1 Hz, 1H), 4.65 (bs, 3H), 4.27 (m, 2H), 4.15 (d, J=8.4 Hz, 1H), 3.97 (m, 2H), 3.84 (d, J=6.9 Hz, 1H), 3.45 (d, J=4.8 Hz, 1H), 2.78 (m, 1H), 2.33 (s, 6H), 2.25 (d, J=8.7 Hz, 2H), 2.17 (s, 3H), 2.10 (s, 3H), 1.96 (s, 3H), 1.83 (m, 1H), 1.74 (s, 3H), 1.62 (s, 1H), 1.48 (m, 2H), 1.19 (m, 5H), 0.83 (t, J=7.2 Hz, 3H); $^{13}C$ NMR ($CDCl_3$, 75.5 Hz) δ201.9, 172.3, 170.5, 169.2, 167.0, 156.3, 140.1, 138.4, 133.8, 133.4, 130.2, 129.2, 129.0, 128.9, 128.7, 128.2, 126.8, 125.3, 83.9, 81.4, 78.8, 77.3, 76.0, 75.6, 74.6, 74.1, 73.7, 72.2, 65.4, 57.5, 56.5, 47.2, 43.2, 35.4, 26.6, 22.6, 21.5, 21.0, 18.9, 15.1, 14.7, 13.7, 10.9.

FABMS (NOBA) M+H calcd for $C_{47}H_{60}NSO_{15}$: 910. Found: 910. Anal. calcd for $C_{47}H_{59}NSO_{15}$: C, 62.03; H, 6.53; N, 1.54. Found: C, 62.16; H, 6.45; N, 1.57.

EXAMPLE 3

3'-N-debenzoyl-3'-N-(t-butoxycarbonyl)-7-O-methylthiomethyl-3'-isobutenylpaclitaxel

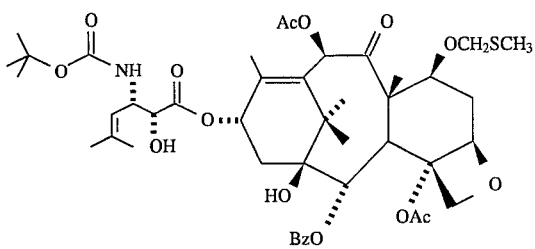

To a solution of 7-O-methylthiomethylbaccatin III (1.5 g, 2.3 mmol) in 30 mL of THF was added n-BuLi (1.0 mL, 2.5M in hexane, 2.5 mmol) at −60° C. and stirred for 10 minutes. Then a solution of (±)-cis-3-triethylsilyloxy-4-isobutenyl-N-(t-butoxycarbonyl)azetidin-2-one (3.3 g, 9.3 mmol) in 10 mL of THF was added dropwise. The solution was then stirred at 0° C. for 30 min. and quenched with sat. NH$_4$Cl solution and extracted with ethyl acetate. The solution was dried over MgSO$_4$ and concentrated and the residue chromatographed over silica gel (3:1 hexane/ethyl acetate). The product was dissolved in 100 mL of THF and was shaken with Bu$_4$NF (2.3 mL, 1.0M in THF, 2.3 mmol) diluted with ethyl acetate and washed with brine. The solution was dried over MgSO$_4$ and concentrated and the residue chromatographed over silica gel (1.5:1 hexane/ethyl acetate) to give 1.6 g of the title product (78%); IR(film) 3452 (br), 1724, 1370, 1242, 1096, 1066 cm$^{-1}$; $^1$H NMR (CDCl$_3$,300 MHz) δ8.0 7 (d, J=7.2 Hz, 2H), 7.59 (t, J=7.5 Hz, 1H), 7.45 (t, J=7.8 Hz, 2H), 6.54 (s, 1H), 6.11 (t, J=9.3 Hz, 1H), 5.66 (d, J=6.0 Hz, 1H), 5.29 (d, J=6.0 Hz, 1H), 4.94 (d, J=8.1 Hz, 1H), 4.75 (m, 2H), 4.64 (ABq, J=12.0, 2.7 Hz, 2H), 4.29 (m, 2H), 4.20 (m, 2H), 3.86 (d, J=6.0 Hz, 1H), 3.37 (bd, 1H), 2.79 (m, 1H), 2.35 (s, 6H), 2.16 (s, 3H), 2.10 (s, 3H), 2.04 (s, 3 H), 1.82 (m, 1H), 1.74 (s, 9H), 1.34 (s, 9H), 1.23 (s, 3H), 1.20 (s, 3H); $^{13}$C NMR (CDCl$_3$,75.5 Hz) δ202, 170.2, 169.2, 166.9, 155.4, 140.6, 138.0, 133.7, 133.1, 130.1, 129.2, 128.6, 120.6, 83.8, 81.2, 79.9, 78.7, 77.2, 76.1, 75.5, 74.6, 74.0, 73.7, 72.2, 57.4, 51.5, 47.1, 43.2, 35.4, 32.9, 28.2, 26.4, 25.8, 22.4, 21.0, 18.6, 15.1, 14.8, 10.9.

FABMS (NOBA) M+H calcd for C$_{45}$H$_{62}$NSO$_{15}$: 888. Found: 888.

EXAMPLE 4

(3R, 4R)-3-Triethylsilyloxy-4-(2-furyl)-N-(n-butyl-oxycarbonyl)azetidin- 2-one

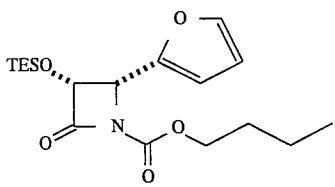

(3R,4R)-3-Triethylsilyloxy-4-(2-furyl)azetidin-2-one (0.58 g, 2.17 mmol) in 30 mL of dichloromethane was stirred with diisopropylethyl amine (0.4 mL, 2.30 mmol) and butylchloroformate (0.3 mL, 2.36 mmol) in addition to a catalytic amount of DMAP (N,N-dimethylaminopyridine). The solution was stirred for 1 h and diluted with dichloromethane and washed with brine, dried over MgSO$_4$ and concentrated. The residue was chromatographed over silica gel (eluted with 3:1 hexane/ethyl acetate) to give 523 mg of product (Y: 65%); IR(KBr) 1820, 1734, 1318, 1018, 734 cm$^{-1}$; $^1$H NMR (CDCl$_3$,300 MHz) δ 7.38 (m, 1H), 6.35 (m, 2H), 5.09 (ABq, J=15.5, 5.6 Hz, 2H), 4.14 (m, 2H), 1.56 (m, 2H), 1.28 (s, 2H), 0.87 (t, J=8.7 Hz, 3H), 0.82 (t, J=7.9, 9H), 0.50 (m, 6H); $^{13}$C NMR (CDCl$_3$,75.5 Hz) δ165.4, 149.1, 147.6, 142.9, 110.5, 109.9, 77.7, 66.6, 55.9, 30.5, 18.8, 13.6, 6.3, 4.3; DCIMS M+H calcd for C$_{18}$H$_{29}$NO$_5$Si: 368, Found: 368.

EXAMPLE 5

(3R, 4R)-3-Triethylsilyloxy-4-(2-furyl)-N-isopropyl-oxycarbonylazetidin- 2-one

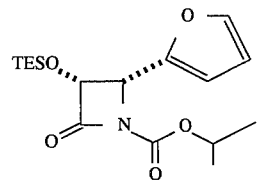

(3R, 4R)-3-Triethylsilyloxy-4-(2-furyl)azetidin-2-one (0.51 g, 1.91 mmol) in 25 mL of dichloromethane was stirred with diisopropylethyl amine (0.78 mL, 4.4 mmol) and i-propylchloroformate (4.0 mL, 1.0M in toluene, 4.0 mmol) in addition to a catalytic amount of DMAP. The solution was stirred for 1 h and diluted with dichloromethane and washed with brine, dried over MgSO$_4$ and concentrated. The residue was chromatographed over silica gel (eluted with 5:1 hexane/ethyl acetate) to give 649 mg of the title product (Y: 96%); IR(KBr) 1822, 1812, 1716, 1374, 1314, 1186, 1018, 1004, 746 cm$^{-1}$; $^1$H NMR (CDCl$_3$, 300MHz) δ7.39 (m, 1H), 6.35 (m, 2H), 5.08 (ABq, J=15.6, 5.6 Hz, 2H), 4.96 (d, J=10.0 Hz, 1H), 1.25 (d, J=6.3 Hz, 3H), 1.17 (d, J=6.3 Hz, 3H)), 0.83 (t, J=7.8, 9H), 0.50 (m, 6H); $^{13}$C NMR (CDCl$_3$,75.5 Hz) δ165.5, 148.6, 147.8, 142.9, 110.5, 109.9, 77.6, 71.1, 55.9, 21.7, 21.6, 6.3, 4.4; DCIMS M+H calcd for C$_{17}$H$_{28}$NO$_5$Si: 354, Found: 354.

EXAMPLE 6

(±)-cis-3-Triethylsilyloxy-4-isobutenyl-N-t-butoxy-carbonylazetidin- 2-one (a) preparation of N-(4-methoxy)-N-(3-methyl-2-butenyl)benzenamine

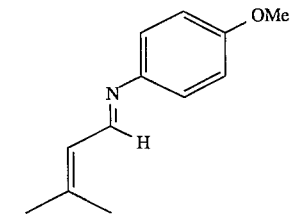

A solution of p-anisidine (5.7 g, 46.3 mmol) was dissolved in diethylether (100 mL) and was treated with a catalytic amount of p-toluensulfonic acid (10 mg). To this was added 3-methyl-2-butenal (2.67 mL, 50.9 mmol) in one portion and the reaction was allowed to stir at ambient temperature for 16 h. The solvent was then evaporated on a rotary evaporator at 0.5 torr to furnish the desired imine (8.7 g, 100%) as a brown oil; $^1$H NMR 300 MHz, CDCl$_3$): δ8.38

(d, 1H, J=9.5 Hz), 7.11 (dd, 2H, J=2.2, 6.7 Hz), 6.88 (dd, 2H, J=2.2, 6.7 Hz), 6.22–6.18 (m, 1H), 3.81 (s, 3H), 2.01 (s, 3H), 1.95 (s, 3H).

(b) preparation of (±)-cis-N-(4-methoxyphenyl)-3-acetyloxy-4-isobutenylazetidin-2-one

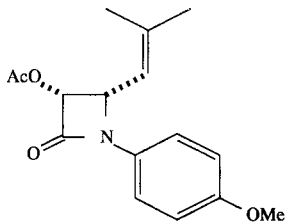

A solution of acetoxyacetyl chloride (6.9 g, 50.5 mmol) was dissolved in ethyl acetate (100 mL) and cooled to −30° C. under an inert atmosphere. To this solution was added triethylamine (7.0 mL, 50.5 mmol) over a 5 min period. The resulting white slurry was then treated with an ethyl acetate solution of N-4-methoxy-N-(3-methyl-2-butenyl)benzenamine (8.7 g, 40 mL) dropwise over a 20 min period. The resulting green-brown slurry was then gradually allowed to warm to ambient temperature over a 4 h period. The slurry was then filtered through a pad of celite and the filtrate was washed with water then brine. The organic fraction was dried (MgSO$_4$) and concentrated to give a brown oil. The crude product was purified by careful silica gel chromatography (eluted with hexanes/ethyl acetate 8:2) to furnish an orange oil which solidified on standing. This was recrystallized from dichloromethane/hexanes to furnish the desired product as a pale yellow solid (4.4 g, 32%); 1H NMR (300 MHz, CDCl$_3$): δ7.32 (d, 2H, J=9.1 Hz), 6.86 (d, 2H, J=9.1 Hz), 5.59 (dd, 1H, J=3.0, 7.8 Hz), 5.14–5.10 (m, 1H), 4.96 (dd, 1H, J=4.8, 9.3 Hz), 3.77 (s, 3H), 2.11 (s, 3H,), 1.81 (s, 3H), 1.78 (s, 3H).

(c) preparationn of (±)-cis-3-Acetyloxy-4-isobutenylazetidin-2-one

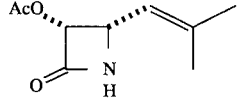

A solution of the (±)-cis-N-(4-methoxyphenyl)-3-acetyloxy-4-isobutenylazetidin-2-one (4.88 g, 16.2 mmol) was dissolved in acetonitrile (50 mL) and cooled to 0°–5° C. in an ice bath. To this was added a cold solution of ceric ammonium nitrate (26.6 g, 48.6 mmol, 50 mL) in one portion. The deep red reaction was allowed to stir for 10 min and during that time the color gradually lightened to orange. The cold solution was transferred to a separatory funnel, diluted with water, and extracted with ethyl acetate. The organic fraction was washed with several portions of 10% aqueous sodium sulfite, followed by saturated aqueous sodium bicarbonate. The organic fraction was dried (MgSO$_4$) and concentrated to give the desired product (2.71 g, 91%) as a yellow-orange solid that was used directly in the next step; 1H NMR (300 MHz, CDCl$_3$): δ6.11 (bs, 1H), 5.73 (dd, 1H, J=2.2, 4.7 Hz), 5.12–5.08 (m, 1H), 4.63 (dd, 1H, 4.7, 9.1 Hz), 2.09 (s, 3H), 1.75 (s, 3H), 1.67 (s, 3H).

(d) preparation of (±)-cis-3-Triethylsilyloxy-4-isobutenylazetidin-2-one

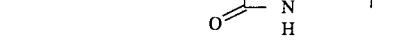

(±)-cis-3-Acetyloxy-4-isobutenylazetidin-2-one (1.47 g, 8.0 mmol) was dissolved in methanol (15 mL) and was stirred with K$_2$CO$_3$ (110.5 mg, 0.8 mmol) for 3 h at ambient temperature. The solution was then neutralized with Dowex 50W-X8 resin and then filtered. The filtrate was concentrated and the crude solid was dissolved in THF (25 mL) and cooled to 5° C. in an ice bath. Imidazole (544.0 mg, 8.0 mmol) was added and once dissolved, triethylsilyl chloride (1.34 mL, 8.0 mmol) was added dropwise via syringe. The resulting slurry was allowed to warm to ambient temperature and stir overnight. The solution was filtered and the filtrate was washed with water, then brine. The organic fraction was dried (MgSO$_4$) and concentrated. The crude solid was purified by silica gel chromatography (eluted with hexanes/ethyl acetate 3:1) to furnish the desired product (612 mg, 30%) as a pale yellow solid; 1H NMR (300 MHz, CDCl$_3$): δ5.87 (bs, 1H), 5.31–5.2 6 (m, 1H), 4.90 (dd, 1H, J=2.2, 4.7 Hz), 4.42 (dd, 1H, J=4.7, 9.3 Hz), 1.74 (s, 3H), 1.28 (s, 3H), 0.98–0.91 (m, 9H), 0.71–0.55 (m, 6H).

(e) preparation of (±)-cis-3-Triethylsilyloxy-4-isobutenyl-N-t-butoxycarbonylazetidin-2-one

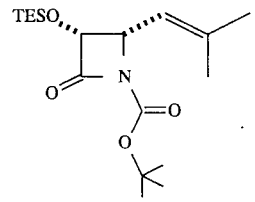

(±)-cis-3-Triethylsilyloxy-4-isobutenylazetidin-2-one (1.01 g, 3.95 mmol) was dissolved in dichloromethane (20 mL) and was treated with diisopropylethylamine (0.68 mL, 3.95 mmol) and a catalytic amount of dimethylaminopyridine. To this solution was added di-t-butyl dicarbonate (1.02 g, 4.68 mmol) and the solution was allowed to stir for 24 h at ambient temperature. The solution was then diluted with additional dichloromethane and washed with water then brine. The organic fraction was dried (MgSO$_4$) and concentrated. The residue was purified by silica gel chromatography (eluted with hexanes/ethyl acetate 8:2) to give the desired product (1.26 g, 90%) as a colorless oil; 1H NMR (300 MHz, CDCl$_3$): δ5.24 (d, 1H, J=9.6 Hz), 4.86 (d, 1H, J=5.7 Hz), 4.72 (dd, 1H, J=6.0, 9.9 Hz), 1.78 (d, 3H, J=1.1 Hz), 1.75 (d, 3H, J=1.1 Hz), 1.47 (s, 9H), 0.96–0.9 1 (m, 9H), 0.64–0.55 (m, 6H).

EXAMPLE 7

3'-N-Debenzoyl-3'-desphenyl-3'-N-(isopropyloxy-carbonyl)-3'-(2-furyl)-7-O-methylthiomethylpaclitaxel

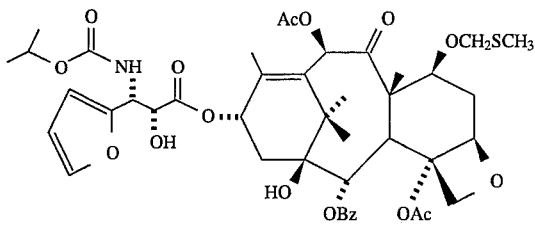

To a solution of the 7-O-methylthiomethylbaccatin III (2.0 g, 3.1 mmol) in 40 mL of THF at −60° C. was added LiHMDS (3.7 mL, 1.0M, 3.7 mmol) followed by (3R, 4R)-3-triethylsilyloxy-4-(2-furyl)-N-isopropyloxycarbony-lazetidin- 2-one (883 mg, 2.40 mmol) in 25 mL of THF after stirring 10 min. (4.05 g, 11.5 mmol). The solution was brought to 0° C. and stirred for 30 min. The solution was quenched with saturated $NH_4Cl$ and extracted with ethyl acetate, dried over $MgSO_4$ and concentrated. The residue was chromatographed over silica gel (2.5:1 hexane/ethyl acetate) to give 2.8 g of silyl ether. The silyl ether was dissolved in 30 mL of THF as stirred 10 min with $Bu_4NF$ (3.0 mL, 1.0M, 3 mmol) diluted with ethyl acetate and washed with brine. The organic fraction was dried ($MgSO_4$), concentrated and the residue purified over silica gel (1:1 hexane/ethyl acetate) to give 2.0 g of the title product (72%); IR(film) 3448 (br), 1718, 1372, 1240, 1108, 1066 cm$^{-1}$; $^1$H NMR (CDCl$_3$, 300 MHz) δ8.08 (d, J=7.2 Hz, 2H), 7.58 (m, 1H), 7.46 (t, J=7.5 Hz, 2H), 7.39 (s, 1H), 6.53 (s, 1H), 6.36(m, 1H), 6.31 (m, 1H), 6.20 (t, J=8.1 Hz, 1H), 5.66 (d, J=6.9 Hz, 1H), 5.34 (s, 2H), 4.92 (d, J=7.8 Hz, 1H), 4.79 (m, 1H), 4.70 (m, 1H), 4.65 (ABq, J=12, 3.6 Hz, 2H), 4.29 (m, 2H), 4.15 (d, J=8.4 Hz, 1H), 3.86 (d, J=6.9 Hz, 1H), 3.39 (br s, 1H), 2.77 (m, 1H), 2.38 (s, 3H), 2.30 (m, 2H), 2.17 (s, 3H), 2.10 (s, 3H), 2.02 (s, 3H), 1.83 (m, 1H), 1.74 (s, 3H), 1.72 (s, 1H), 1.20–1.10 (m, 12H); $^{13}$C NMR (CDCl$_3, 75.5$ Hz) δ201.8, 170.4, 169.2, 167.0, 142.5, 140.2, 133.7, 133.4, 130.2. 129.1, 128.6, 110.7, 107.6, 83.9, 81.3, 78.7, 77.2, 76.1, 75.5, 74.6, 74.0, 72.3, 71.8, 69.1, 57.5, 51.9, 47.2, 43.2, 35.3, 32.9, 26.5 22.5, 22.0, 21.9, 20.9, 15.1, 14.6, 10.9.

HRFABMS (NOBA) M+H calcd for $C_{44}H_{56}NO_{16}S$: 886.3320. Found: 886.3345.

EXAMPLE

2'-O-[(Methylthiomethoxy)methyl]paclitaxel

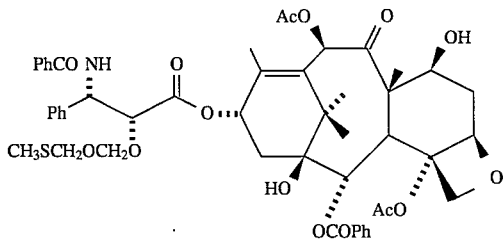

Palladium (10%) on carbon (3 g) was added to a solution of 2'-O-methylthiomethoxymethyl-7-O-benzyloxycarbon-ylpaclitaxel (1.2 g, 1.11 mmol) in ethyl acetate (100 mL) and ethanol (70 mL) housed in a Parr bottle. The vessel was affixed to a Parr apparatus and the reaction mixture subjected to hydrogen at 50 psi. The reaction mixture was shaken for 20.5 h, then filtered using a sintered glass funnel. The filtrate was concentrated in vacuo and the residual oil purified via flash chromatography (eluted with hexanes: ethyl acetate) to provide the desired (0.98 g, 93%) as a solid. $^1$H NMR (CDCl$_{3, 300}$ MHz) δ8.128– 8.10 (2H, m), 7.76–7.73 (2H, m), 7.61–7.27 (11H, m), 7.03 (1H, d, J=8.9 Hz), 6.40–6.27 (1H, m), 6.25 (1H, s), 5.80 (1H, dd, J =8.9, 2.4 Hz), 5.66 (1H, d, J=7.1 Hz), 4.98–4.94 (1H, m), 4.86–4.79 (2H, m), 4.75–4.68 (1H, m), 4.43–4.39 (1H, m), 4.31–4.26 (2H, m), 4.05 (1H, d, J=11.7 Hz), 3.78 (1H, d, J =7.1 Hz), 2.60–1.06 (25H, m, including singlets at 2.45, 2.21, 2.02, 1.85, 1.66, 1.22, 1.11, 3H each).

EXAMPLE 9

2'-O-(Methylthiomethoxy)methyl-7-O-methylthio-methylpaclitaxel

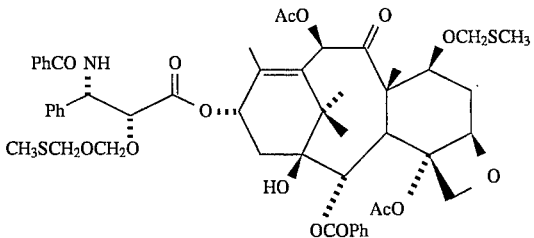

To a solution of 2'-O-[(methylthiomethoxy)methyl]pacli-taxel. (0.98 g, 1.03 mmol) and dimethyl sulfide (0.6 mL, 8.11 mmol) in acetonitrile (20 mL) cooled to −40° C. was added benzoyl peroxide (1.0 g, 4.13 mmol) and the reaction mixture was warmed to room temperature over 30 min. At this time a TLC analysis (eluted with hexanes: ethyl acetate, 1:1) indicated the reaction was complete. The reaction mixture was then diluted with ethyl acetate and the resulting organic solution was washed three times with a saturated sodium bicarbonate solution then brine. The organic phase was then dried over sodium sulfate and concentrated in vacuo. The residual oil was purified via flash chromatography (eluted with hexanes: ethyl acetate) to provide the title product (0.945 g, 91%) as a white solid; $^1$H NMR (CDCl$_3$, 300 MHz) δ8.13–8.11 (2H, m), 7.79–7.77 (2H, m), 7.61–7.29 (11H, m), 6.54 (1H, s), 6.30–6.26 (1H, m), 5.83–5.80 (1H, m), 5.71–5.69 (1H, m), 5.01–4.66 (6H, m), 4.34–4.04 (5H, m), 3.88 (1H, d, J=6.6 Hz), 2.90–2.80 (1H, m), 2.55–1.05 (27H, m, including singlets at 2.51, 2.18, 2.11, 1.80, 1.21, 11.20, 3H each).

EXAMPLE 10

2'-O-Triethylsilyl-7-O-methylthiomethylpaclitaxel

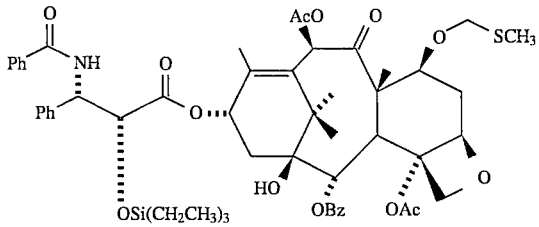

To a solution of 2'-O-triethylsilylpaclitaxel (20.1 g, 20.8 mmol) in mL of acetonitrile was added dimethylsulfide (16 mL, 216 mmol) and the solution cooled to 0° C. At 0° C.

benzoyl peroxide (20.2 g, 83.5 mmol) was added and the solution stirred for 90 minutes. The reaction mixture was diluted with ethyl acetate and washed with NaHCO$_3$ and then brine. The solution was dried over MgSO$_4$ and concentrated and the residue chromatographed over silica gel (2:1 hexane/ethyl acetate) to give 20.4 g of product (95%); $^1$H NMR (CDCl$_3$, 300 MHz) δ8.11 (d, J=6.9 Hz, 2H), 7.73 (d, J=6.9 Hz, 2H), 7.60–7.23 (m, 11H), 7.11 (d, J=8.7 Hz, 1H), 6.5 (s, 1H), 6.22 (t, J=9.3 Hz, 1H), 5.69 (d, J=7.5 Hz, 2H), 4.95 (d, J=8.1 Hz, 1H), 4.68 (d, J=2.0 Hz, 1H), 4.65 (s, 1H), 4.27 (m, 3H), 3.88 (d, J=6.9 Hz, 1H), 2.80 (m, 1H), 2.52 (s, 3H), 2.39 (m, 1H), 2.16 (s, 3H), 2.10 (s, 3H), 2.04 (s, 3H), 1.85 (m, 2H), 1.75 (s, 3H), 1.19 (s, 3H), 1.17 (s, 3H), 0.80 (t, J=7.8 Hz, 9H), 0.43 (m, 6H); IR(KBr) 3442, 1724, 1242, 1066 cm$^{-1}$.

Anal. Calcd. for C$_{55}$H$_{69}$NSiSO$_{14}$: C, 64.24; H, 6.76; N, 1.36. Found: C, 63.87; H, 6.70; N, 1.31. FABMS (NOBA) M+Na calcd for C$_{55}$H$_{69}$NSiSO$_{14}$: 1050. Found: 1050.

EXAMPLE 11

7-O-[[(Chloroacetyl)oxy]methoxy]paclitaxel

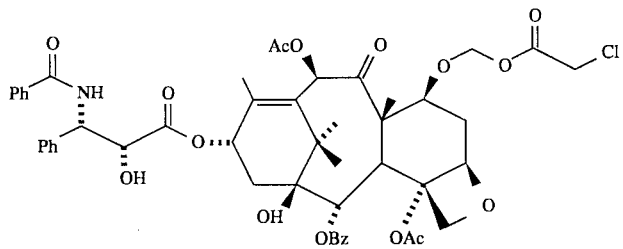

To a solution of the 2'-O-triethylsilyl-7-O-methylthiomethylpaclitaxel (20 g, 19.4 mmol) in 200 mL of THF along with 4A sieves was added chloroacetic acid (7.4 g, 78.7 mmol). After stirring the mixture for 10 minutes NIS (5 g, 22.2 mmol) and silver triflate were added (750 mg, 2.9 mmol). After 20 minutes the reaction mixture was filtered through Celite, diluted with ethyl acetate and washed with NaHCO$_3$ and 10% Na$_2$S$_2$O$_3$. The solution was then washed several times with NaHCO$_3$ and finally with brine. The solution was dried over MgSO$_4$ and concentrated and the residue chromatographed over silica gel (1:1 hexane/ethyl acetate) to give 9.5 g of product (51%); 1H NMR (CDCl$_3$, 300 MHz)δ8.09 (d, J=7.2 Hz, 2H), 7.74 (d, J=7.2 Hz, 2H), 7.62–7.30 (m, 11H), 7.04 (d, J=8.8 Hz, 1H), 6.33 (s, 1H), 6.17 (t, J=8.1 Hz, 1H), 5.77 (dd, J=9.0, 2.4 Hz, 1H), 5.64 (d, J=6.9 Hz, 1H), 5.47 (d, J=6.6 Hz, 1H), 5.22 (d, J=6.6 Hz, 1H), 4.90 (d, J=8.1 Hz, 1H), 4.7 7 (s, 1H), 4.28 (m, 2H), 4.10 (m, 1H), 4.07 (s, 2H), 3.80 (d, J=6.9 Hz, 1H), 3.64 (br s, 1H), 2.70 (m, 1H), 2.36 (s, 3H), 2.30 (d, J=9.0 Hz, 2H), 2.18 (s, 3H), 1.90 (m, 1H), 1.82 (s, 3H), 1.73 (s, 3H), 1.67 (br s, 3H), 1.18 (s, 6H); IR(KBr) 3448, 1724, 1244, 1106 cm$^{-1}$.

Anal. Calcd. for C$_{50}$H$_{54}$NO$_{16}$Cl: C, 62.53; H, 5.67; N, 1.46. Found: C, 62.42; H, 5.89; N, 1.31.

FABMS (NOBA) M+Na calcd for C$_{50}$H$_{54}$NO$_{16}$Cl: 982. Found: 982.

EXAMPLE 12

7-O-[[[(4-methyl-1-piperaznyl)acetyl]oxy]methoxy]-paclitaxel (Ia)

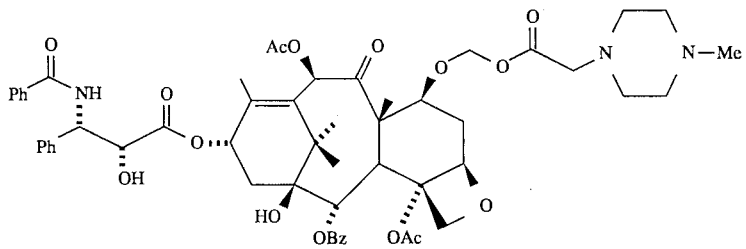

To a solution of 7-O-[[(chloroacetyl)oxy]methoxy]paclitaxel (3.2 g, 3.33 mmol) in 200 mL of acetone was added NaI (1.5 g, 10.0 mmol) and stirred at ambient temperature for 1 hour. To the reaction mixture was added methylpiperazine (1.7 mL, 15.3 mmol) and stirred for 2 hours. The solution was filtered through Celite, concentrated and the residue dissolved in ethyl acetate and washed with water (3X) and brine. The solution was dried over MgSO$_4$ and concentrated and the residue chromatographed over silica gel (15% acetonitrile/10% methanol/75% methylene chloride) to give 2.06 g of pure free base (60%). Hydrochloride salt To the free base in 40 mL of ethyl acetate was added HCl in ethyl acetate (0.53M, 6.0 mL, 3.6 mmol). The salt was filtered off and dried under reduced pressure to give 1.8 g (52%); IR(KBr) 3428, 1722, 1244, 1110 cm$^{-1}$; $^1$H NMR (d$_6$ acetone/D$_2$O, 300 MHz)δ8.06 (d, J=7.2 Hz, 2H), 7.95 (d, J=7.2 Hz, 2H), 7.66–7.22 (m, 11H), 6.37 (s, 1H), 6.08 (br t, 1H), 5.66 (d, J=6.0 Hz, 1H), 5.61 (d, J=7.2 Hz, 1H), 5.36 (dd, J=12.6, 7.2 Hz, 2H), 4.97 (d, J=8.4 Hz, 1H), 4.81 (d, J=6.0 Hz, 1H), 4.29 (m, 1H), 4.14 (d, J=7.2 Hz, 1H), 4.12 (s, 1H), 4.03 (d, J=7.2 Hz, 1H), 3.97 (d, J=4.5 Hz, 1H), 3.79 (d, J=6.9 Hz, 1H), 2.99 (s, 4H), 2.73 (m, 1H), 2.39 (s, 3H), 2.38–2.10 (m, 7H), 1.92 (s, 3H), 1.81 (m, 1H), 1.65 (s, 3H), 1.1 6 (s, 3H), 1.13 (s, 3H).

FABMS (NOBA) M+H calcd for $C_{55}H_{66}N_3O_{18}$: 1024. Found: 1024.

Citrate salt

To the free base (2.0 g, 1.95 mmol) in 60 mL of ethyl acetate was added citric acid as a 0.499 M solution in acetone/ethyl acetate 1:1 (4.0 mL, 1.99 mmol). The salt was removed by filtration and dried under reduced pressure to give 1.8 g of salt which was combined with another batch and recrystalized from hot ethyl acetate with a minimal amount of acetone to dissolve the salt followed by addition of hexane and cooling. Citrate thus obtained was>94% pure by HPLC.

EXAMPLE 13

7-O-[(N,N-diethylaminoacetyl)oxy]methoxy]paclitaxel (Ib)

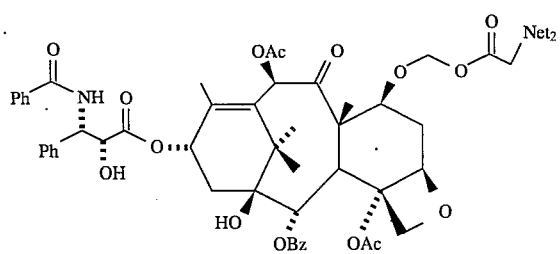

To a solution of the bromoacetyl ester, made analogous to the chloroacetyl ester of Example 11, (7.0 g, 6.97 mmol) in 200 mL of acetone was added NaI (1.0 g, 6.6 mmol) followed by diethylamine (7.2 mL, 70 mmol). The reaction was stirred for 2 hours, filtered through Celite and concentrated. The residue was diluted with ethyl acetate and washed with water and brine. The solution was dried over MgSO$_4$ and concentrated and the residue chromatographed over silica gel (1:1 hexane/ethyl acetate 5% methanol) to give 4.61 g of the free base (66%).

Methanesulfonate salt

To the free base (1.36 g, 1.37 mmol) in 10 mL of ethyl acetate was added methanesulfonic acid (0.5M in ethyl acetate, 2.9 mL, 1.45 mmol). The salt was removed by filtration and dried under reduced pressure (1.32 g, 88%); IR(KBr) 3428, 1726, 1242, 1108 cm$^{-1}$; $^1$H NMR (CDCl$_3$, 300 MHz)δ10.74 (br s, 1H), 8.06 (d, J=6.9 Hz, 2H), 7.85 (d, J=6.9 Hz, 2H), 7.73 (d, J=8.4 Hz, 1H), 7.63–7.23 (m, 11H), 6.39 (s, 1H), 6.10 (t, J=8.4 Hz, 1H), 5.71 (dd, J=8.7, 3.3 Hz, 1 H), 5.63 (d, J=6.9 Hz, 1H), 5.39 (ABq, J=19.2, 6.3 Hz, 2H), 4.91 (d, J=8.7 Hz, 1H), 4.79 (d, J=3.3 Hz, 1H), 4.42 (dd, J=10.8, 6.6 Hz, 1H), 4.28 (d, J=8.4 Hz, 1H), 4.14 (m, 3H), 3.78 (d, J=6.9 Hz, 1H), 3.38 (m, 4H), 2.69 (s, 3H), 2.63 (m, 1H), 2.34 (s, 3H), 2.20 (m, 2H), 2.17 (s, 3H), 1.96 (s, 3H), 1.81 (m, 2H), 1.71 (s, 3H), 1.37 (q, J=6.9 Hz, 6H), 1.16 (s, 3H), 1.15 (s, 3H).

Anal. Calcd. for $C_{55}H_{68}N_2O_{19}S$: C, 60.43; H, 6.27; N, 2.56. Found: C, 60.10; H, 6.33; N, 2.56. FABMS (NOBA) M+H calcd for $C_{54}H_{65}N_2O_{16}$: 997. Found: 997.

Hydrochloride salt

The free base (1.33 g, 1.34 mmol) in 12 mL of ethyl acetate was treated with HCl in ethyl acetate (2M, 0.7 mL, 1.40 mmol) and the salt filtered off and dried under reduced pressure to give 1.1 g of the hydrochloride (79%); IR(KBr) 3428, 1726, 1242, 1108 cm$^{-1}$; $^1$H NMR (CDCl$_3$,300 MHz) d 12.2 (br s, 1H), 8.09 (d, J=7.2 Hz, 2H), 7.83 (d, J=6.9 Hz, 2H), 7.65–7.27 (m, 12H), 6.34 (s, 1H), 6.10 (t, J=8.4 Hz, 1H), 5.73 (dd, J=5.7, 3.6 Hz, 1H), 5.63 (d, J=6.9 Hz, 1H), 5.43 (d, J=6.6 Hz, 1H), 5.32 (d, J=6.3 Hz, 1H), 4.90 (d, J=8.7 Hz, 1H), 4.81 (d, J=3.6 Hz, 1H), 4.30 (m, 2H), 4.14 (d, J=6.9 Hz, 1H), 3.97 (br s, 2H), 3.78 (d, J=6.6 Hz, 1H), 3.33 (m, 4H), 2.60 (m, 1H), 2.39 (s, 3H), 2.20 (s, 3H), 2.19 (m, 2H), 1.87 (s, 3H), 1.80 (m, 2H), 1.71 (s, 3H), 1.40 (q, J=6.9 Hz, 6H), 1.17 (s, 3H), 1.15 (s, 3H).

Anal. Calcd. for $C_{54}H_{65}N_2O_{16}Cl \cdot H_2O$: C, 61.67; H, 6.42; N, 2.66. Found: C, 61.49; H, 6.32; N, 2.61. FABMS (NOBA) M+H calcd for $C_{54}H_{65}N_2O_{16}$: 997. Found: 997.

EXAMPLE 14

7-O-[(methylthiomethoxy)methyl]paclitaxel

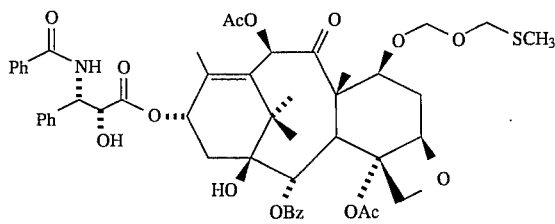

To a solution of 2'-O-triethylsilylpaclitaxel (5.07 g, 5.24 mmol) in 100 mL of THF with 4 A sieves was added bisthiomethylmethyl ether (5.13 g, 37.2 mmol). To this solution was added NIS (2.36 g, 10.5 mmol) followed by silver triflate (385 mg, 1.49 mmol). After stirring the reaction for 1 hour the solution was filtered through Celite, diluted with ethyl acetate and washed with saturated NaHCO$_3$ and 10% Na$_2$S$_2$O$_3$. The solution was washed twice with saturated NaHCO$_3$ and then brine. The solution was dried over MgSO$_4$ and concentrated and the residue chromatographed over silica gel (2:1 hexane/ethyl acetate) to give 1.7 g of the extended thioacetal with the 2'TES group removed (34%); IR(KBr) 3440, 1724, 1242, 1106, 1020 cm$^{-1}$; $^1$H NMR (CDCl$_3$,300 MHz)δ8.09(d, J=6.9 Hz, 2H), 7.7 5 (d, J=6.9 Hz, 2H), 7.61–7.24 (m, 11H), 7.04 (d, J=9.0 Hz, 1H), 6.31 (s, 1H), 6.16 (t, J=7.5 Hz, 1H), 5.78 (dd, J=9.0, 2.4 Hz, 1H), 5.64 (d, J=6.9, 1H), 4.94 (d, J=7.5 Hz, 1H), 4.90 (d, J=8.4 Hz, 1H), 4.77 (d, J=2.4 Hz, 1H), 4.71 (d, J=7.5 Hz, 1H), 4.59 (ABq, J=11.7, 6.0 Hz, 2H), 4.28 (d, J=8.4 Hz, 1H), 4.16 (d, J=8.4 Hz, 1H), 4.10 (m, 1H), 3.81 (d, J=6.9 Hz, 1H), 2.79 (m, 1H), 2.35 (s, 3H), 2.29 (d, J=9.0 Hz, 2H), 2.18 (s, 3H), 2.11 (s, 3H), 1.91 (m, 1H), 1.79 (s, 3H), 1.73 (s, 3H), 1.65 (m, 2H), 1.18 (s, 6H). FABMS (NOBA) M+Na calcd for $C_{50}H_{57}NO_{15}S$: 966. Found: 966.

EXAMPLE 15

7-O-[[[Chloroacetyl)oxy]methoxy]methoxy]paclitaxel

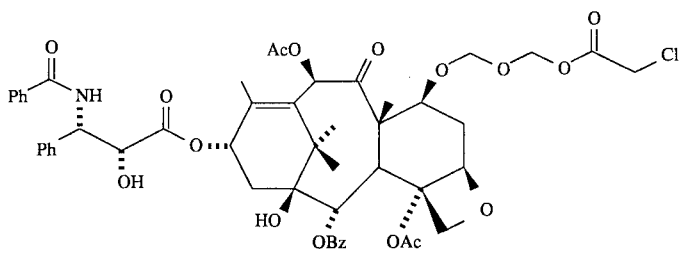

To a solution of 7-O-[(methylthiomethoxy)methyl]paclitaxel (16.78 g, 17.7 mmol) in 200 mL of THF with 4 Å sieves was added chloroacetic acid (6.78 g, 72.4 mmol). To this solution was added NIS (4.85 g, 21.5 mmol) followed by silver triflate (190 mg, 0.74 mmol). After stirring the reaction for 20 minutes the solution was filtered through Celite, diluted with ethyl acetate and washed with saturated NaHCO$_3$ and 10% Na$_2$S$_2$O$_3$. The solution was washed twice with saturated NaHCO$_3$ and then brine. The solution was dried over MgSO$_4$ and concentrated and the residue chromatographed over silica gel (5:1 methylene chloride/ethyl acetate) to give 4.0 g of the chloroacetyl ester (23%); IR(KBr) 3444, 1722, 1240, 1110 cm$^{-1}$; $^1$H NMR (CDCl$_3$, 300 MHz)δ8.10 (d, J=7.5 Hz, 2H), 7.76 (d, J=7.2 Hz, 2H), 7.63–7.25 (m, 11H), 7.05 (d, J=8.7 Hz, 1H), 6.31 (s, 1H), 6.17 (br t, 1H), 5.79 (d, J= 6.3 Hz, 1H), 5.65 (d, J=6.9, 1H), 5.42 (d, J=8.4 Hz, 2H), 5.35 (ABq, J=16.2, 6.3 Hz, 2H), 4.90 (d, J=8.1 Hz, 1H), 4.77 (s, 1H), 4.30 (d, J=8.4 Hz, 1H), 4.17 (d, J=8.4 Hz, 1H), 4.11 (m, 3H), 3.81 (d, J=6.6 Hz, 1H), 2.76 (m, 1H), 2.36 (s, 3H), 2.34 (d, J=13.2 Hz, 2H), 2.20 (s, 3H), 2.16 (s, 1H), 1.90 (m, 2H), 1.81 (s, 3H), 1.74 (s, 3H), 1.67 (m, 1H), 1.10 (s, 6H).

FABMS (NOBA) M+Li calcd for C$_{51}$H$_{56}$NO$_{17}$Cl: 996. Found: 996.

EXAMPLE 16

7-O-[[[[(4-Methyl-1-piperazinyl)acetyl]oxy]methoxy]methoxy]paclitaxel (Ic)

N-methyl piperazine (3.5 mL, 31.5 mmol) was added. The reaction was stirred for 4 hours, filtered through Celite and concentrated. The residue was diluted with ethyl acetate and washed with water and then brine. The solution was dried over MgSO$_4$ and concentrated and the residue chromatographed over silica gel (15% acetonitrile/7% methanol/78% methylene chloride) to give 2.185 g of product; IR(KBr) 3432, 1722, 1244, 1112 cm$^{-1}$; $^1$H NMR (300 MHz, d$_6$ Acetone/D$_2$O)δ8.06 (d, J=7.2 Hz, 2H), 7.95 (d, J=7.2 Hz, 2H), 7.66–7.22 (m, 11H), 6.37 (s, 1H), 6.08 (br t, 1H), 5.66 (d, J=6.0 Hz, 1H), 5.61 (d, J=7.2 Hz, 1H), 5.36 (dd, J=12.6, 7.2 Hz, 2H), 4.97 (d, J=8.4 Hz, 1H), 4.81 (d, J=6.0 Hz, 1H), 4.29 (m, 1H), 4.14 (d, J=7.2 Hz, 1H), 4.12 (s, 1H), 4.03 (d, J=7.2 Hz, 1H), 3.97 (d, J=4.5 Hz, 1H), 3.79 (d, J=6.9 Hz, 1H), 2.99 (s, 4H), 2.73 (m, 1H), 2.39 (s, 3H), 2.38–2.10 (m, 7H), 1.92 (s, 3H), 1.81 (m, 1H), 1.65 (s, 1H), 1.16 (s, 3H), 1.13 (s, 3H).

Hydrochloride salt

The free base in 200 mL of ethyl acetate was treated with HCl in ethyl acetate (0.53M, 4.0 mL, 2.12 mmol) and the hydrochloride filtered off and dried under reduced pressure to give 2.10 g of hydrochloride (48%).

FABMS (NOBA) M+H calcd for C$_{56}$H$_{68}$N$_3$O$_{17}$: 1054. Found: 1054.

EXAMPLE 17

7-O-[[(Morpholinoacetyl)oxy]methoxy]paclitaxel (Id)

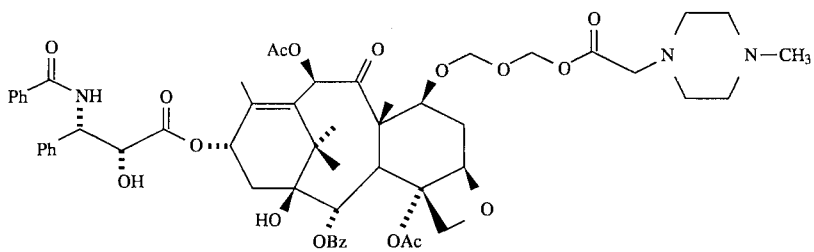

To a solution of 7-O-[[[chloroacetyl)oxy]methoxy]methoxy]paclitaxel (4.0 g, 4.0 mmol) in 80 mL of acetone was added NaI (1.2 g, 8.0 mmol). After stirring for 1 hour

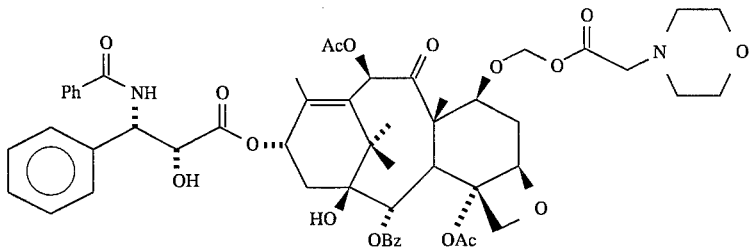

The title compound was prepared analogous to the method described for compound Ia in 69% yield and precipitated as the methanesulfonic acid salt; $^1$H NMR (300 MHz, CDCl$_3$) δ8.06 (d, J=7.2 Hz, 2H), 7.82 (d, J=7.2 Hz, 2H), 7.62–7.26 (m, 12H), 6.38 (s, 1H), 6.10 (br t, 1H), 5.66 (d, J=4.8 Hz, 1H), 5.63 (d, J=6.9 Hz, 1H), 5.40 (ABq, J=14.1, 6.3 Hz, 2H), 4.91 (br d, J=8.4 Hz, 1H), 4.80 (d, J=3.6 Hz, 1H), 4.35 (m, 1H), 4.28 (d, J=8.4 Hz, 1H), 4.15–3.99 (m, 10H), 3.76 (d, J=6.9 Hz, 1H), 3.56 (m, 1H), 3.37 (m, 2H), 2.70 (m, 1H), 2.35 (s, 3H), 2.17 (m, 5H), 1.92 (s, 3H), 1.82 (m, 1H), 1.71 (m, 3H), 1.16 (s, 6H); HPLC purity>95%; IR (KBr) 3436, 1724, 1244, 1112, 1044 cm$^{-1}$.

Ion Spray MS M+H calcd. for $C_{54}H_{63}N_2O_{17}$: 1011. Found: 1011.

EXAMPLE 18

7-O-[[(N,N-dimethylaminoacetyl)oxy]methoxy]-paclitaxel (Ie)

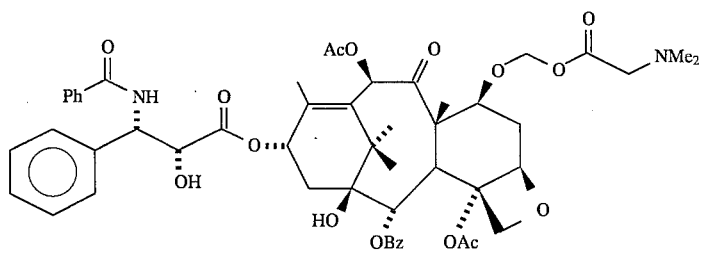

The title compound was prepared analogous to the method described for compound Ia in 45% yield and precipitated as the methanesulfonic acid salt; $^1$H NMR (300 MHz, CDCl$_3$) δ8.08 (d, J=7.2 Hz, 2H), 8.00 (d, J=7.2 Hz, 2H), 7.70–7.23 (m, 12H), 6.38 (s, 1H), 6.12 (t, J=8.1 Hz, 1H), 5.65 (dd, J=9.6, 6.0 Hz, 2H), 5.43 (s, 2H), 4.96 (d, J=8.1 Hz, 1H), 4.86 (d, J=6.0 Hz, 1H), 4.37 (m, 1H), 4.33 (s, 2H), 4.14 (s, 2H), 3.81 (d, J=6.9 Hz, 1H), 3.12 (s, 6H), 3.10 (m, 2H), 2.77 (m, 1H), 2.59 (s, 3H), 2.39 (s, 3H), 2.27 (m, 1H), 2.22 (s, 3H), 2.20 (m, 1H), 1.95 (s, 3H), 1.82 (m, 1H), 1.74 (s, 3H), 1.20 (s, 3H), 1.18 (s, 3H); HPLC purity>94%; IR (KBr) 3436, 1724, 1242, 1110 cm$^{-1}$.

Ion Spray MS M+H calcd. for $C_{52}H_{61}N_2O_{16}$: 969. Found: 969.

EXAMPLE 19

2-O-[[[[(4-Methyl-1-piperazinyl)acetyl]oxy]methoxy]-methoxy]paclitaxel (If)

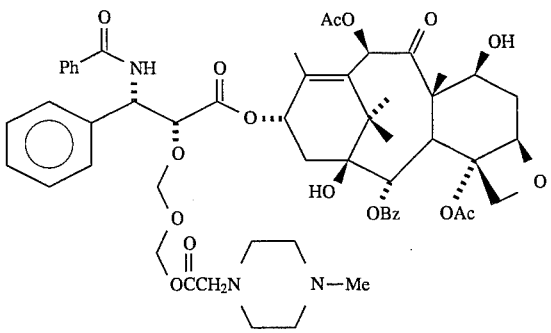

The title compound was prepared analogous to the method described for compound Ia in 53% yield and precipitated as the hydrochloric acid salt; $^1$H NMR (300 MHz, d$_6$ acetone/D$_2$O)δ8.08 (d, J=6.9 Hz, 2H), 7.96 (d, J=6.9 Hz, 2H), 7.69–7.22 (m, 12H), 6.40 (s, 1H), 6.08 (t, J=8.7 Hz, 1H), 5.72 (d, J=7.2 Hz, 1H), 5.62 (d, J=7.2 Hz, 2H), 5.30 (ABq, J=18.6, 6.6 Hz, 2H), 5.17 (s, 1H), 4.94 (d, J=8.7 Hz, 1H), 4.32 (m, 1H), 4.12–4.00 (m, 4H), 3.56 (br m, 12H), 2.96 (s, 3H), 2.42 (m, 1H), 2.42 (s, 3H), 2.25 (m, 2H), 2.14 (s, 3H), 1.91 (s, 3H), 1.80 (m, 1H), 1.62 (s, 3H), 1.15 (s, 6H); HPLC purity 90%; IR (KBr) 3428, 1720, 1246, 1070 cm$^{-1}$.

FABMS M+H calcd. for $C_{56}H_{68}N_3O_{17}$: 1054. Found: 1054.

In vivo antitumor activity

Balb/c×DBA$_2$ F$_1$ (CDF$_1$) hybrid mice were implanted subcutaneously (sc) with 0.1 ml of a 2% (w/v) brei of M109 lung carcinoma as described in W. Rose "Evaluation of Madison 109 Lung Carcinoma as a Model for Screening Antitumor Drugs," *Cancer Treatment Rep*, 65, No. 3–4 pp. 299–312 (1981). The test compounds and reference drug, paclitaxel, were administered intravenously to groups of mice; each group received a compound at a different dose level, and three or four different dose levels were evaluated per compound. Mice were followed daily for survival until their death or about day 75 post-tumor implant, whichever occurred first. One group of mice per experiment remained untreated and served as the control. Tumors were also measured once or twice weekly and the size in mm was used to estimate tumor weight according to the published procedure (ibid).

Median survival times of compound-treated (T) mice were compared to the median survival time of parallel control (C) mice. The ratio of the two values for each compound-treated group of mice was multiplied by 100 and expressed as a percentage (i.e., % T/C) in Table I for representative compounds. Additionally, the difference between the median time for treated groups and that for the control group to grow tumor to 1 gm, expressed at T–C values in days, is also shown in Table I. The greater the T–C value, the greater the delay in primary tumor growth. Compounds showing % T/C>125% and/or T–C>4.0 days are considered to be active in this M109 SC model.

TABLE I

| Compound | Maximum Effect | | Opt. Dose (mg/kg/inj;) |
|---|---|---|---|
| | % T/C | T-C(days) | |
| Ia | >177 | 25.3 | 24[a] |
| Ib | 129 | 13.5 | 16/36[b] |
| Id | 173 | 12.0 | 30[a] |
| Ie | 165 | 11.3 | 45[a] |

[a]Compound was administered i.v. once daily, on days 4, 5, 6, 7 and 8 post-tumor implant.
[b]Compound was administered i.v. once daily, on days 5, 6, 7, 8 and 9 post-tumor implant.

We claim:

1. A compound of the formula (I):

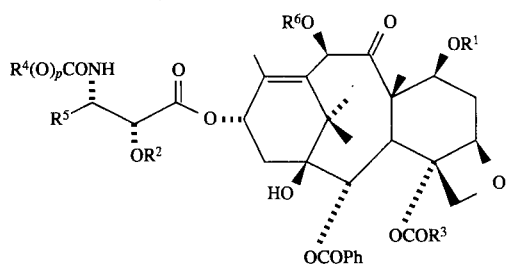

wherein $R^1$ or $R^2$ are independently hydrogen or $-(CH_2O))_nCOCH_2Y$; $R^6$ is hydrogen, $C_{1-8}$ alkanoyl or $-(CH_2O)_nCOCH_2Y$; n is one to six; p is zero or one; $R^4$ and $R^5$ are independently $C_{1-8}$ alkyl, $C_{2-8}$ alkenyl, $C_{2-8}$ alkynyl, or $-Z-R^7$; Z is a direct bond, $C_{1-8}$ alkylene or $C_{2-8}$ alkenediyl; $R^7$ is aryl, substituted aryl, $C_{3-8}$ cycloalkyl or heteroaryl; $R^3$ is hydrogen, $C_{1-8}$ alkyl, $C_{2-8}$ alkenyl, $C_{2-8}$ alkynyl, $C_{3-8}$ cycloalkyl, aryl or heteroaryl; Y is a radical of the formula

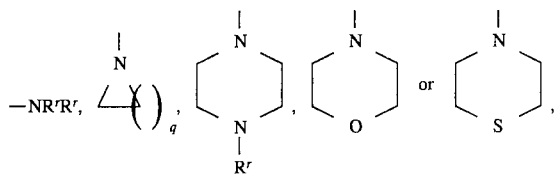

in which q is one to three; $R^r$ is hydrogen or $C_{1-8}$ alkyl; and with the proviso at least one of $R^1$, $R^2$ and $R^6$ is $-(CH_2O)_nCOCH_2Y$; or a pharmaceutically acceptable salt thereof.

2. A compound of claim 1 in which $R^6$ is acetyl; $R^2$ is hydrogen; $R^4$ is phenyl; p is zero; $R^5$ is phenyl; and $R^3$ is methyl.

3. The compound of claim 2 that is 7-O-[[[-(4-methyl-1-piperaznyl)acetyl]oxy]methoxy]paclitaxel.

4. The compound of claim 2 that is 7-O-[-(N,N-diethlaminoacetyl)oxy]methoxy]paclitaxel.

5. The compound of claim 2 that is 7-O-[[[[-(4-methyl-1-piperazinyl)acetyl]oxy]methoxy]methoxy]paclitaxel.

6. The compound of claim 2 that is 7-O-[[(morpholinoacetyl)oxy]methoxy]paclitaxel.

7. The compound of claim 2 that is 7-O-[-(N,N-dimethylaminoacetyl)oxy]methoxy]paclitaxel.

8. A compound of claim 1 in which $R^6$ is acetyl; $R^1$ is hydrogen; $R^4$ is phenyl; p is zero; $R^5$ is phenyl; and $R^3$ is methyl.

9. The compound of claim 8 that is 2'-O-[[[[-(4-methyl-1-piperazinyl)acetyl]oxy]methoxy]methoxy]paclitaxel.

10. A pharmaceutical composition which comprises an antitumor effective amount of a compound of claim 1 and a pharmaceutically acceptable carrier.

11. A method for inhibiting tumor growth in a mammalian host which comprises administering to said mammal a tumor-growth inhibiting amount of a compound of a claim 1.

* * * * *